United States Patent
Segall et al.

(10) Patent No.: US 8,343,566 B2
(45) Date of Patent: Jan. 1, 2013

(54) PREPARATION OF CANOLA PROTEIN ISOLATE WITHOUT HEAT TREATMENT ("C200CA")

(75) Inventors: Kevin I. Segall, Winnipeg (CA); Brent E Green, Warren (CA); Martin Schweizer, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 595 days.

(21) Appl. No.: 12/542,922

(22) Filed: Aug. 18, 2009

(65) Prior Publication Data

US 2010/0040763 A1 Feb. 18, 2010

Related U.S. Application Data

(60) Provisional application No. 61/136,193, filed on Aug. 18, 2008.

(51) Int. Cl.
*A23J 1/00* (2006.01)

(52) U.S. Cl. ......................... 426/656; 426/634; 424/725

(58) Field of Classification Search ................... 426/656
See application file for complete search history.

(56) References Cited

U.S. PATENT DOCUMENTS

| | | | |
|---|---|---|---|
| 2,762,820 A | 9/1956 | Sugarman | |
| 4,131,607 A | 12/1978 | Petit | |
| 4,151,310 A | 4/1979 | Mattil et al. | |
| 4,208,323 A | 6/1980 | Murray | |
| 4,307,118 A | 12/1981 | Kajs | |
| 4,889,921 A | 12/1989 | Diosady et al. | |
| 5,086,166 A | 2/1992 | Lawhon et al. | |
| 5,844,086 A | 12/1998 | Murray | |
| 6,005,076 A | 12/1999 | Murray | |
| 6,630,195 B1 | 10/2003 | Muralidhara | |
| 6,720,020 B2 | 4/2004 | Karleskind et al. | |
| 7,309,773 B2 | 12/2007 | Green et al. | |
| 2003/0015910 A1 | 1/2003 | Ichikawa | |
| 2003/0125526 A1 | 7/2003 | Barker et al. | |
| 2004/0034200 A1 | 2/2004 | Logie et al. | |
| 2004/0039174 A1 | 2/2004 | Barker et al. | |
| 2004/0077838 A1 | 4/2004 | Green et al. | |
| 2004/0254353 A1 | 12/2004 | Barker et al. | |
| 2005/0181112 A1 | 8/2005 | Schweizer et al. | |
| 2005/0249828 A1 | 11/2005 | Logie et al. | |
| 2007/0065567 A1 * | 3/2007 | Segall et al. | 426/634 |
| 2009/0311397 A1 * | 12/2009 | Whalen et al. | 426/436 |

FOREIGN PATENT DOCUMENTS

| WO | WO 02/089597 | 11/2002 |
|---|---|---|
| WO | WO 03/043439 | 5/2003 |
| WO | WO 03/053157 | 7/2003 |

* cited by examiner

*Primary Examiner* — Elizabeth Gwartney

(74) *Attorney, Agent, or Firm* — Michael I. Stewart; Sim & McBurney

(57) ABSTRACT

The supernatant from the deposition of canola protein micellar mass is processed to provide a canola protein isolate which is soluble in an aqueous acidic environment.

37 Claims, No Drawings

PREPARATION OF CANOLA PROTEIN ISOLATE WITHOUT HEAT TREATMENT ("C200CA")

REFERENCE TO RELATED APPLICATION

This application claims priority under 35 USC 119(e) from U.S. Provisional Patent Application No. 61/136,193 filed Aug. 18, 2008.

FIELD OF INVENTION

The present invention relates to the production of a canola protein isolate.

BACKGROUND TO THE INVENTION

Canola oil seed protein isolates having protein contents of at least 100 wt % (N×6.25) can be formed from oil seed meal by a process as described in copending U.S. patent application Ser. No. 10/137,391 filed May 3, 2002 (U.S. Patent Application Publication No. 2003-0125526 A1 and WO 02/089597) and U.S. patent application Ser. No. 10/476,230 filed Jun. 9, 2004 (U.S. Patent Application Publication No. 2004-0254353 A1), assigned to the assignee hereof and the disclosures of which are incorporated herein by reference. The procedure involves a multiple step process comprising extracting canola oil seed meal using an aqueous salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous, gluten-like protein micellar mass (PMM), and recovering the protein micellar mass from supernatant having a protein content of at least about 100 wt % (N×6.25). As used herein, protein content is determined on a dry weight basis. The recovered PMM may be dried.

In one embodiment of the process, the supernatant from the PMM settling step is processed to recover canola protein isolate from the supernatant. This procedure may be effected by initially concentrating the supernatant using an ultrafiltration membrane and drying the concentrate. The resulting canola protein isolate has a protein content of at least about 90 wt %, preferably at least about 100 wt % (N×6.25).

The procedures described in U.S. patent application Ser. No. 10/137,391 are essentially batch procedures. In copending U.S. patent application Ser. No. 10/298,678 filed Nov. 19, 2002 (U.S. Patent Application Publication No. 2004-0039174 A1 and WO 03/043439) and U.S. patent application Ser. No. 10/496,071 filed Mar. 5, 2005 (U.S. Patent Application Publication No. 2003-0015910 A1), assigned to the assignee hereof and the disclosures of which are incorporated herein by reference, there is described a continuous process for making canola protein isolates. In accordance therewith, canola oil seed meal is continuously mixed with an aqueous salt solution, the mixture is conveyed through a pipe while extracting protein from the canola oil seed meal to form an aqueous protein solution, the aqueous protein solution is continuously conveyed through a selective membrane operation to increase the protein content of the aqueous protein solution to at least about 50 g/L, while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is recovered from the settling vessel and may be dried. The PMM has a protein content of at least about 90 wt % (N×6.25), preferably at least about 100 wt %. The overflowed supernatant may be processed to recover canola protein isolate therefrom, as described above.

Canola seed is known to contain about 10 to about 30 wt % proteins and several different protein components have been identified. These proteins include a 12S globulin, known as cruciferin, a 7S protein and a 2S storage protein, known as napin. As described in copending U.S. patent application Ser. No. 10/413,371 filed Apr. 15, 2003 (U.S. Patent Application Publication No. 2004-0034200 A1 and WO 03/088760) and U.S. patent application Ser. No. 10/510,766 filed Apr. 29, 2005 (U.S. Patent Application Publication No. 2005-0249828 A1), assigned to the assignee hereof and the disclosures of which are incorporated herein by reference, the procedures described above, involving dilution of concentrated aqueous protein solution to form PMM and processing of supernatant to recover additional protein, lead to the recovery of isolates of different protein profiles.

In this regard, the PMM-derived canola protein isolate has a protein component composition of about 60 to about 98 wt % of 7S protein, about 1 to about 15 wt % of 12S protein and 0 to about 25 wt % of 2S protein. The supernatant-derived canola protein isolate has a protein component composition of about 60 to about 95 wt % of 2S protein, about 5 to about 40 wt % of 7S protein and 0 to about 5 wt % of 12S protein. Thus, the PMM-derived canola protein isolate is predominantly 7S protein and the supernatant-derived canola protein isolate is predominantly 2S protein. As described in the aforementioned U.S. patent application Ser. No. 10/413,371, the 2S protein has a molecular mass of about 14,000 daltons, the 7S protein has a molecular mass of about 145,000 daltons and the 12S protein has a molecular mass of about 290,000 daltons.

In copending U.S. patent application Ser. No. 11/038,086 filed Jan. 21, 2005 (U.S. Patent Publication No. 2005-0181112 A1 and WO 2005/067729) and Ser. No. 12/213,500 filed Jun. 20, 2008 assigned to the assignee hereof and the disclosures of which are incorporated herein by reference, there is described a procedure wherein the supernatant is heat-treated to deposit 7S protein and provide an aqueous protein solution enriched in 2S protein. This aqueous protein solution may be dried to provide a 2S-enriched canola protein isolate. This canola protein isolate has many benefits, including solubility over a wide range of acid pH values and clarity in aqueous medium, making it possible, for example, to prepare protein fortified beverages, particularly at acid pH values, in which the clarity is not impaired by the addition of the canola protein isolate.

Canola is also known as rapeseed or oil seed rape.

SUMMARY OF INVENTION

It has now been found that a product of equivalent properties to those of the 2S protein enriched canola protein isolate can be prepared without the heat treatment step. Eliminating the heat treatment step serves to improve colour and taste and increases overall yield since 7S proteins need not be removed from the supernatant. The resulting canola protein isolate is not only completely soluble, transparent and heat stable in water at low pH but also generally low in phytic acid. Heat stability in solution at low pH permits thermal processing such as hot fill applications. The canola protein isolate is useful in products for human consumption, such as for the protein fortification of, in particular, soft drinks and sports drinks, as well as other aqueous systems, without precipitation of protein. The canola protein isolate is also useful for non-human food applications such as pet foods and aquaculture.

In accordance with one aspect of the present invention, there is provided a process of preparing a canola protein isolate having a protein content of at least about 90 wt % (N×6.25) on a dry weight basis, which comprises:

adding a calcium salt, preferably calcium chloride, to supernatant from the precipitation of a canola protein micellar mass to provide a conductivity of about 5 mS to about 30 mS, preferably about 8 to about 10 mS, to form calcium phytate precipitate, removing precipitated calcium phytate from the resulting solution to provide a clear solution, optionally adjusting the pH of the clear solution to about 2.0 to about 4.0, preferably about 2.9 to about 3.2, such as by the addition of hydrochloric acid, concentrating the optionally pH-adjusted clear solution to a protein content of at least about 50 g/L, preferably about 50 to about 500 g/L, more preferably about 100 to about 250 g/L, to produce a clear concentrated canola protein solution, optionally diafiltering the clear concentrated canola protein solution, such as with volumes of pH 3 water, optionally effecting a colour removal step, such as a granular activated carbon treatment, and drying the concentrated protein solution.

The supernatant may be partially concentrated to an intermediate concentration prior to addition of the calcium salt. The precipitate which forms is removed and the resulting solution is acidified as described above, further concentrated to the final concentration and then optionally diafiltered and dried.

Alternatively, the supernatant first may be concentrated to the final concentration, the calcium salt is added to the concentrated supernatant, the resulting precipitate is removed and the solution is acidified and then optionally diafiltered and dried.

In another variation of the above-described process, initially a small amount of calcium salt is added to the supernatant such that no precipitate is formed, the solution is acidified and partially concentrated to an intermediate concentration, an additional amount of calcium salt is added to the partially concentrated supernatant and a precipitate forms.

The precipitate is removed and the solution is concentrated to its final concentration and optionally diafiltered and dried.

It is an option in the above-described procedures to omit the removal of the precipitate, which leads to a higher phytate content in the product. In such procedure, the calcium salt is added to supernatant, partially concentrated supernatant or fully concentrated supernatant and the precipitate is not removed. Acidification leads to resolubilization of the precipitate.

A further option is to omit the acidification and effect processing of the solution at natural pH. In this option calcium salt is added to supernatant, partially concentrated supernatant or concentrated supernatant to form a precipitate which is removed. The resulting solution then is processed as described above without the acidification step.

Where the supernatant is partially concentrated prior to the addition of the calcium salt and fully concentrated after removal of the precipitate, the supernatant is first concentrated to a protein concentration of about 50 g/L or less, and, after removal of the precipitate, then is concentrated to a concentration of at least about 50 g/L, preferably about 50 to about 500 g/L, more preferably about 100 to about 250 g/L.

In one embodiment of the invention, the calcium salt may be added in two stages. In this embodiment, a small amount of calcium is added to the supernatant to provide a conductivity of about 1 mS to about 3.5 mS, preferably about 1 mS to about 2 mS, which is insufficient to cause the formation of a precipitate.

The resulting solution is acidified and partially concentrated under the conditions described above. The balance of the calcium salt is added to the partially concentrated solution to provide a conductivity of about 4 mS to about 30 mS, preferably about 4 to about 10 mS, to result in the formation of a precipitate. The precipitate then is removed. The resulting clear solution then is concentrated under the conditions described above.

The canola protein isolate produced according to the process herein may be used in conventional applications of protein isolates, such as, protein fortification of processed foods and beverages, emulsification of oils, body formers in baked goods and foaming agents in products which entrap gases. In addition, the canola protein isolate may be formed into protein fibers, useful in meat analogs, may be used as an egg white substitute or extender in food products where egg white is used as a binder. The canola protein isolate may be used as nutritional supplements. Other uses of the canola protein isolate are in pet foods, animal feed and in industrial and cosmetic applications and in personal care products.

GENERAL DESCRIPTION OF THE INVENTION

The initial step of the process of providing the canola protein isolate involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.05, preferably at least about 0.10, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In view of the greater degree of dilution required for protein precipitation with increasing ionic strengths, it is usually preferred to utilize an ionic strength value less than about 0.8, and more preferably a value of about 0.1 to about 0.15.

In a batch process, the salt solubilization of the protein is effected at a temperature of from about 5° C. to about 75° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 75° C. is chosen due to the denaturation temperature of some of the present proteins.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure is effected at temperatures between about 10° C. and about 75° C., preferably between about 15° C. and about 35° C.

The aqueous food grade salt solution generally has a pH of about 5 to about 6.8, preferably about 5.3 to about 6.2. The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a first fat removal step is carried out, the salt generally is added after completion of such operations.

Another alternative procedure is to extract the oil seed meal with the food grade salt solution at a relatively high pH value above about 6.8, generally up to about 9.9. The pH of the food grade salt solution may be adjusted to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing decanter centrifugation, followed by disc centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution is concentrated to increase the protein concentration thereof while maintaining the ionic strength thereof substantially constant. Such concentration generally is effected to provide a concentrated protein solution having a protein concentration of at least about 50 g/L, preferably at least about 200 g/L, more preferably at least about 250 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass through the membrane while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contaminants are removed from the aqueous protein solution by passage through the membrane with the permeate. The diafiltration operation may be effected until no significant further quantities of contaminants and visible colour are present in the permeate. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour adsorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5% to about 5% w/v, preferably about 2% to about 3% w/v, may be used. The colour adsorbing agent may be removed from the canola protein solution by any convenient means, such as by filtration.

The concentrated and optionally diafiltered protein solution resulting from the optional colour removal step may be subjected to pasteurization to reduce the microbial load. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

Depending on the temperature employed in the concentration step and optional diafiltration step and whether or not a pasteurization step is effected, the concentrated protein solution may be warmed to a temperature of at least about 20°, and up to about 60° C., preferably about 25° to about 40° C., to decrease the viscosity of the concentrated protein solution to facilitate performance of the subsequent dilution step and micelle formation. The concentrated protein solution should not be heated beyond a temperature above which micelle formation does not occur on dilution by chilled water.

The concentrated protein solution resulting from the concentration step, and optional diafiltration step, optional colour removal step, optional pasteurization step and optional defatting step, then is diluted to effect micelle formation by mixing the concentrated protein solution with chilled water having the volume required to achieve the degree of dilution desired. Depending on the proportion of canola protein desired to be obtained by the micelle route and the proportion from the supernatant, the degree of dilution of the concentrated protein solution may be varied. With lower dilution levels, in general, a greater proportion of the canola protein remains in the aqueous phase.

When it is desired to provide the greatest proportion of the protein by the micelle route, the concentrated protein solution is diluted by about 5 fold to about 25 fold, preferably by about 10 fold to about 20 fold.

The chilled water with which the concentrated protein solution is mixed has a temperature of less than about 15° C., generally about 1° to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous sticky gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution of the concentrated protein solution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel. In lieu of settling by sedimentation, the PMM may be separated continuously by centrifugation.

The combination of process parameters of concentrating of the protein solution to a preferred protein content of at least about 200 g/L and the use of a dilution factor of about 10 to about 20, result in higher yields, often significantly higher yields, in terms of recovery of protein in the form of protein micellar mass from the original meal extract, and much purer isolates in terms of protein content than achieved using any of the known prior art protein isolate forming procedures discussed in the aforementioned US patents.

By the utilization of a continuous process for the recovery of canola protein isolate as compared to the batch process, the initial protein extraction step can be significantly reduced in time for the same level of protein extraction and significantly higher temperatures can be employed in the extraction step. In addition, in a continuous operation, there is less chance of contamination than in a batch procedure, leading to higher product quality and the process can be carried out in more compact equipment.

The settled PMM is separated from the residual aqueous phase or supernatant, such as by decantation of the residual aqueous phase from the settled mass or by centrifugation. The PMM may be used in the wet form or may be dried, by any convenient technique, such as spray drying or freeze drying, to a dry form. The dry PMM has a high protein content, in excess of about 90 wt % protein, preferably at least about 100 wt % protein (calculated as N×6.25), and is substantially undenatured (as determined by differential scanning calorimetry). The dry PMM isolated from fatty oil seed meal also has a low residual fat content, when the procedures of U.S. Pat. Nos. 5,844,086 and 6,005,076 are employed as necessary, which may be below about 1 wt %.

As described in the aforementioned U.S. patent application Ser. No. 10/413,371, the PMM consists predominantly of a 7S canola protein having a protein component composition of about 60 to 98 wt % of 7S protein, about 1 to about 15 wt % of 12S protein and 0 to about 25 wt % of 2S protein.

The supernatant from the PMM formation and settling step contains significant amounts of canola protein, not precipitated in the dilution step, and is processed to recover canola protein isolate therefrom. As described in the aforementioned U.S. patent application Ser. No. 10/413,371, the canola protein isolate derived from the supernatant consists predominantly of 2S canola protein, having a protein component composition of about 60 to about 95 wt % of 2S protein, about 5 to about 40 wt % of a 7S protein and 0 to about 5 wt % of 12S protein.

In the present invention, a calcium salt, preferably calcium chloride, is added to the supernatant, which may first be concentrated or partially concentrated in the manner described below, to provide a conductivity of about 5 mS to about 30 mS, preferably 8 mS to about 10 mS. The calcium chloride added to the supernatant may be in any desired form, such as a concentrated aqueous solution thereof.

The addition of the calcium chloride has the effect of depositing phytic acid, in the form of calcium phytate, from the supernatant and retaining both globulin and albumin fractions of the supernatant. The deposited phytate is recovered from the supernatant, such as by centrifugation and/or filtration to leave a clear solution. If desired, the deposited phytate may not be removed in which case the further processing results in a product having a higher phytate content.

The pH of the solution then is adjusted to a value of about 2.0 to about 4.0, preferably about 2.9 to 3.2. The pH adjustment may be effected in any convenient manner, such as by the addition of hydrochloric acid. If desired, the acidification step may be omitted from the various options described herein.

The pH-adjusted clear solution, if not already concentrated, is concentrated to increase the protein concentration thereof. Such concentration is effected using any convenient selective membrane technique, such as ultrafiltration, using membranes with a suitable molecular weight cut-off permitting low molecular weight species, including salt, carbohydrates, pigments and other low molecular weight materials extracted from the protein source material, to pass through the membrane, while retaining a significant proportion of the canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the supernatant in this way also reduces the volume of liquid required to be dried to recover the protein. The supernatant generally is concentrated to a protein concentration of at least about 50 g/L, preferably about 50 to about 500 g/L, more preferably about 100 to about 250 g/L, prior to drying. Such concentration operation may be carried out in a batch mode or in a continuous operation, as described above for the protein solution concentration step.

Where the supernatant is partially concentrated prior to the addition of the calcium salt and fully concentrated after removal of the precipitate, the supernatant is first concentrated to a protein concentration of about 50 g/L or less, and, after removal of the precipitate, then is concentrated to a concentration of at least about 50 g/L, preferably about 50 to about 500 g/L, more preferably about 100 to about 250 g/L.

In one embodiment of the invention, the calcium salt may be added in two stages. In this embodiment, a small amount of calcium is added to the supernatant to provide a conductivity of about 1 mS to about 3.5 mS, preferably about 1 mS to about 2 mS, which is insufficient to cause the formation of a precipitate.

The resulting solution is acidified and partially concentrated under the conditions described above. The balance of the calcium salt is added to the partially concentrated solution to provide a conductivity of about 4 mS to about 30 mS, preferably about 4 to about 10 mS, to result in the formation of a precipitate. The precipitate then is removed. The resulting clear solution then is concentrated under the conditions described above.

The concentrated supernatant then may be subjected to a diafiltration step using water. The water may be at its natural pH, a pH equal to the protein solution being diafiltered or any pH in between. Such diafiltration may be effected using from about 2 to about 20 volumes of diafiltration solution, preferably about 5 to about 10 volumes of diafiltration solution. In the diafiltration operation, further quantities of contaminants are removed from the aqueous supernatant by passage through the membrane with the permeate. The diafiltration operation may be effected until no significant further quantities of contaminants and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentrated and optionally diafiltered protein solution may be subjected to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour adsorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5% to about 5% w/v, preferably about 2% to about 3% w/v, may be used. The colour adsorbing agent may be removed from the canola protein solution by any convenient means, such as by filtration.

The concentrated and optionally diafiltered and optionally colour removal treated protein solution is dried by any convenient technique, such as spray drying or freeze drying, to a dry form. The dried canola protein isolate has a high protein content, in excess of about 90 wt % (N×6.25) d.b., preferably at least about 100 wt %, and is substantially undenatured (as determined by differential scanning calorimetry). The canola protein isolate generally is low in phytic acid content, generally less than about 1.5% by weight.

The canola protein isolate produced herein contains both albumin and globulin fractions and is soluble in an acidic aqueous environment, making the isolate ideal for incorporation into beverages, both carbonated and uncarbonated, to provide protein fortification thereto. Such beverages have a wide range of acidic pH values, ranging from about 2.5 to about 5. The canola protein isolate provided herein may be added to such beverages in any convenient quantity to provide protein fortification to such beverages, for example, at least about 5 g of the canola protein isolate per 12 fluid ounce quantity. The added canola protein isolate fully dissolves in the beverage and does not impair the clarity of the beverage, even after thermal processing. The canola protein isolate may be blended with dried beverage prior to reconstitution of the beverage by dissolution in water.

EXAMPLES

Example 1

This Example describes the production of a novel canola protein isolate in accordance with one embodiment of the invention where calcium salt is added to supernatant, the precipitate removed then the solution acidified and further processed.

'a' kg of canola meal was added to 'b' L of 'c' M NaCl solution at ambient temperature and agitated for 30 minutes to provide an aqueous protein solution. The residual canola meal was removed and the resulting protein solution was partially clarified by centrifugation to produce 'd' L of partially clarified protein solution having a protein content of 'e' % by weight. The partially clarified protein solution was filtered to further clarify the protein solution, resulting in a solution of volume 'f' L having a protein content of 'g' % by weight.

A 'h' L aliquot of the protein extract solution was concentrated to 'i' on a polyethersulfone (PES) membrane having a molecular weight cutoff of 'j' Daltons. The resulting concentrated protein solution had a protein content of 'k' % by weight. The concentrated protein solution was pasteurized at 60° C. for 'l' minute(s) to provide 'm' kg of pasteurized, concentrated protein solution with a protein content of 'n' % by weight.

The concentrated solution at 'o' ° C. was diluted 'p' into cold RO water having a temperature 'q' ° C. A white cloud formed immediately and was allowed to settle. The upper diluting water was removed and the precipitated, viscous, sticky mass (PMM) was recovered by centrifugation in a yield of 'r' wt % of the filtered protein solution. The dried PMM derived protein was found to have a protein content of 's' % (N×6.25) d.b. The product was given a designation 't' C307C.

The parameters 'a' to 't' for three runs are set forth in the following Table I:

TABLE I

| t | BW-SA082-F09-08A | BW-SA082-F11-08A | BW-SD084-F18-08A |
|---|---|---|---|
| a | 20 | 20 | 20 |
| b | 200 | 200 | 200 |
| c | 0.15 | 0.15 | 0.15 |
| d | 161 | 164 | 162.5 |
| e | 1.41 | 1.50 | 1.81 |
| f | 172 | 174 | 187.8 |
| g | 1.14 | 1.25 | 1.30 |
| h | 172 | 174 | 187.8 |
| i | 7.45 L | 8.46 kg | 9.24 kg |
| j | 100,000 | 100,000 | 100,000 |
| k | 21.41 | 21.72 | 22.51 |
| l | 1 | 0 | 0 |
| m | 7.9 | | |
| n | 20.11 | | |
| o | 30 | 30 | 29.2 |
| p | 1:15 | 1:15 | 1:15 |
| q | 4 | 4 | 4 |
| r | 49.5 | 48.2 | 59.4 |
| s | 99.31 | 103.34 | 102.09 |

The calcium chloride addition described in the present application was then carried out on the supernatant from the PMM deposition.

'u' L of supernatant was adjusted to conductivity 'v' mS by the addition of calcium chloride. This solution was then centrifuged and/or filtered to remove precipitated phytate material resulting in 'w' L of a reduced phytate content, clarified protein solution at a protein concentration of 'x' % by weight. The reduced phytate content, clarified protein solution was then adjusted to pH 'y' by the addition of HCl and reduced in volume to 'z' L by ultrafiltration using a polyethersulfone (PES) membrane having a molecular weight cut-off of 'aa' Daltons. The concentrate was then diafiltered on the same membrane with 'ab' volumes of pH 3 reverse osmosis purified (RO) water. The diafiltered concentrate contained 'ac' % protein by weight. With the additional protein recovered from the supernatant, the overall protein recovery of the filtered protein solution was 'ad' wt %. A 'ae' L portion of the concentrate was subjected to a colour reduction step by passing it through a 'af' L bed volume (BV) of granular activated carbon at a rate of 'ag' BV/hr at pH 3. The 'ah' L of GAC treated solution having reduced colour and a protein content of 'ai' % by weight was then spray dried and given designation 't' C200CaC. The C200CaC had a protein content of 'aj' (N×6.25) d.b. The remaining 'ak' of concentrate was spray dried without further purification steps to form a final product given designation 't' C200Ca that had a protein content of 'al' % (N×6.25) d.b. The parameters 't' to 'al' for three runs are set forth in the following Table II:

TABLE II

| t | BW-SA082-F09-08A | BW-SA082-F11-08A | BW-SD084-F18-08A |
|---|---|---|---|
| u | 119 | 126 | 137 |
| v | 18.69 | 19.05 | 8.15 |
| w | 115 | 120 | 145 |
| x | 0.54 | 0.57 | 0.35 |
| y | 3.06 | 1.95 | 3.12 |
| z | 5 | 4.5 | 5 |
| aa | 10,000 | 10,000 | 10,000 |
| ab | 5 | 5 | 5 |
| ac | 8.76 | 11.53 | 9.13 |
| ad | 71.9 | 72.0 | 77.0 |
| ae | 2.45 | 2.25 | 0 |
| af | 0.3 | 0.3 | |
| ag | 2.5 | 2.5 | |
| ah | 2.5 | 2.35 | |
| ai | 7.76 | 10.65 | |
| aj | 94.52 | 94.45 | |
| ak | 2.2 L | 2.25 L | 4.74 kg |
| al | 93.52 | 94.04 | 90.36 |

Note
The diafiltered, concentrated treated supernatant from run BW-SA082-F09-08A was polished by filtration before carbon treatment and drying.

Example 2

This Example describes the production of a concentrated canola protein solution that, if dried without further treatment, should produce an isolate in accordance with one embodiment of the invention where the precipitate formed by the addition of calcium salt to supernatant is not removed prior to acidification and further processing.

'a' kg of canola meal was added to 'b' L of 'c' M NaCl solution at ambient temperature and agitated for 30 minutes to provide an aqueous protein solution. The residual canola meal was removed and the resulting protein solution was partially clarified by centrifugation to produce 'd' L of partially clarified protein solution having a protein content of 'e' % by weight. The partially clarified protein solution was filtered to further clarify the protein solution, resulting in a solution of volume 'f' L having a protein content of 'g' % by weight. A 'h' L aliquot of the protein extract solution was concentrated to 'i' kg on a polyethersulfone (PES) membrane having a molecular weight cutoff of 'j' Daltons. The resulting concentrated protein solution had a protein content of 'k' % by weight. The concentrated protein solution was pasteurized at 60° C. for 1 minute to provide 'l' kg of pasteurized, concentrated protein solution containing a protein content of 'm' % by weight.

The pasteurized, concentrated solution at 'n' ° C. was diluted 'o' into cold RO water having a temperature 'p' ° C. A white cloud formed immediately and was allowed to settle. The upper diluting water was removed and the precipitated, viscous, sticky mass (PMM) was recovered by centrifugation in a yield of 'q' wt % of the filtered protein solution. The dried PMM derived protein was found to have a protein content of 'r' % (N×6.25) d.b. The product was given the designation 's' C300.

The parameters 'a' to 's' for one run are set forth in the following Table III:

TABLE III

| s | BW-SA077-A23-08A |
|---|---|
| a | 20 |
| b | 200 |
| c | 0.15 |
| d | 144.5 |
| e | 1.70 |
| f | 150 |
| g | 1.41 |
| h | 150 |
| i | 7.80 |
| j | 100,000 |
| k | 20.88 |
| l | 7.62 |
| m | 20.66 |
| n | 29.6 |
| o | 1:15 |
| p | 3.5 |
| q | 36.3 |
| r | 103.05 |

The calcium chloride addition described in the present application was then carried out on the supernatant from the PMM deposition.

't' L of supernatant with a protein content of 'u' % by weight was adjusted to conductivity 'v' mS by the addition of calcium chloride, resulting in the formation of a haze. The protein solution was then adjusted to pH 'w' by the addition of HCl and the sample cleared. An aliquot of 'x' L of this solution was then reduced in volume to 'y' L by ultrafiltration using a polyethersulfone (PES) membrane having a molecular weight cut-off of 'z' Daltons. The concentrate was then diafiltered on the same membrane with 'aa' volumes of pH 3 RO water. 'ab' kg of diafiltered concentrate was obtained containing 'ac' % protein by weight. With the additional protein recovered from the supernatant, the overall protein recovery of the filtered protein solution was 'ad' wt %. The parameters 's' to 'ad' for one run are set forth in the following Table IV:

TABLE IV

| s | BW-SA077-A23-08A |
|---|---|
| t | 132.5 |
| u | 0.60 |
| v | 18.91 |
| w | 2.97 |
| x | 110 |
| y | 5 |
| z | 10,000 |
| aa | 6 |
| ab | 4.6 |
| ac | 11.08 |
| ad | 60.4 |

Example 3

This Example describes the production of a concentrated canola protein solution that, if dried without further treatment, should produce an isolate in accordance with one embodiment of the invention where the calcium salt is added to partially concentrated supernatant, the precipitate removed and the sample acidified.

'a' kg of canola meal was added to 'b' L of 'c' M NaCl solution at ambient temperature and agitated for 30 minutes to provide an aqueous protein solution. The residual canola meal was removed and the resulting protein solution was partially clarified by centrifugation to produce 'd' L of partially clarified protein solution having a protein content of 'e' % by weight. The partially clarified protein solution was filtered to further clarify the protein solution, resulting in a solution of volume 'f' L having a protein content of 'g' % by weight.

A 'h' L aliquot of the protein extract solution was concentrated to 'i' kg on a polyethersulfone (PES) membrane having a molecular weight cutoff of 'j' daltons. The resulting concentrated protein solution had a protein content of 'k' % by weight.

The concentrated solution at 'l' ° C. was diluted 'm' into cold RO water having a temperature 'n' ° C. A white cloud formed immediately and was allowed to settle. The upper diluting water was removed and the precipitated, viscous, sticky mass (PMM) was recovered by centrifugation in a yield of 'o' wt % of the filtered protein solution. The dried PMM derived protein was found to have a protein content of 'p' % (N×6.25) d.b. The product was given a designation 'q' C302.

The parameters 'a' to 'q' for one run are set forth in the following Table V:

TABLE V

| q | BW-SA082-G30-08A |
|---|---|
| a | 60 |
| b | 600 |
| c | 0.15 |
| d | 440 |
| e | 1.52 |
| f | 505 |
| g | 1.49 |
| h | 505 |
| i | 33.18 |
| j | 100,000 |
| k | 15.66 |
| l | 30.2 |
| m | 1:15 |
| n | 1.8 |
| o | 32.4 |
| p | 101.71 |

The calcium chloride addition described in the present application was then carried out on the partially concentrated supernatant from the PMM deposition.

'r' L of supernatant with a protein content of 's' % by weight was concentrated by ultrafiltration to a volume reduction factor of 7 using a polyethersulfone (PES) membrane having a molecular weight cut-off of 't' Daltons. The partially concentrated supernatant, having a volume of 'u' L and a protein content of 'v' % by weight was then adjusted to a conductivity of 'w' mS by the addition of 3.5% calcium chloride by weight of protein, resulting in the formation of a haze. This solution was then centrifuged and/or filtered to remove precipitated phytate material resulting in 'x' L of a reduced phytate content, clarified, partially concentrated protein solution at a protein content of 'y' % by weight. The reduced phytate content, clarified, partially concentrated protein solution was then adjusted to pH 'z' by the addition of HCl and further concentrated to 'aa' L by ultrafiltration using the same membrane used for the initial concentration of the supernatant. The concentrated solution was then diafiltered on the same membrane with 'ab' volumes of pH 3 RO water. The diafiltered retentate was clear, had a weight of 'ac' kg and a protein content of 'ad' % by weight, resulting in a yield of 'ae' wt % of the filtered protein solution.

The parameters 'r' to 'ae' for one run are set forth in the following Table VI:

TABLE VI

| p | BW-SA082-G30-08A |
|---|---|
| r | 511 |
| s | 0.54 |
| t | 10,000 |
| u | 72 |
| v | 2.70 |
| w | 2.32 |
| x | 72 |
| y | 2.49 |
| z | 3.14 |
| aa | 25 |
| ab | 5.6 |
| ac | 20.24 |
| ad | 8.05 |
| ae | 54.1 |

Example 4

This Example describes the production of a canola protein isolate in accordance with one embodiment of the invention where the calcium salt is added to the supernatant as well as to partially concentrated supernatant, with removal of the precipitate formed after the second addition.

'a' kg of canola meal was added to 'b' L of 'c' M NaCl solution at ambient temperature and agitated for 30 minutes to provide an aqueous protein solution. The residual canola meal was removed and the resulting protein solution was partially clarified by centrifugation to produce 'd' L of partially clarified protein solution having a protein content of 'e' % by weight. The partially clarified protein solution was filtered to further clarify the protein solution, resulting in a solution of volume 'f' L having a protein content of 'g' % by weight.

A 'h' L aliquot of the protein extract solution was concentrated to 'i' on a polyethersulfone (PES) membrane having a molecular weight cutoff of 'j' daltons. The resulting concentrated protein solution had a protein content of 'k' % by weight. The concentrated protein solution was then diafiltered with 'l' volumes of 'c' M NaCl on the same membrane as used for the concentration step. The diafiltered concentrate contained 'm' % protein by weight.

The concentrated solution at 'n' ° C. was diluted 'o' into cold RO water having a temperature 'p' ° C. A white cloud formed immediately and was allowed to settle. The upper diluting water was removed and the precipitated, viscous, sticky mass (PMM) was recovered by centrifugation in a yield of 'q' wt % of the filtered protein solution. The dried PMM derived protein was found to have a protein content of 'r' % (N×6.25) d.b. The product was given a designation 's' C307C.

The parameters 'a' to 's' for two runs are set forth in the following Table VII:

TABLE VII

| s | BW-SD084-H27-08A | BW-SD084-I08-08A |
|---|---|---|
| a | 20 | 60 |
| b | 200 | 600 |
| c | 0.15 | 0.15 |
| d | 159.4 | 495 |
| e | 1.69 | 1.77 |
| f | 170 | 520 |
| g | 1.39 | 1.47 |
| h | 170 | 520 |
| i | 8.25 L | 30 L |
| j | 100,000 | 100,000 |
| k | 21.39 | 21.17 |
| l | 0 | 10 |
| m |  | 21.42 |
| n | 30.1 | 29.9 |
| o | 1:15 | 1:15 |
| p | 7.5 | 4.4 |
| q | 45.3 | 43.4 |
| r | 101.04 | 98.52 |

The calcium chloride addition described in the present application was then carried out on the supernatant and partially concentrated supernatant from the PMM deposition.

't' L of supernatant with a protein content of 'u' % by weight was adjusted to conductivity 'v' mS by the addition of 2.5% calcium chloride per weight of protein and no haze formed. The solution was then adjusted to pH 'w' by the addition of HCl. 'x' L of calcium chloride treated and pH adjusted supernatant was concentrated by ultrafiltration to a volume reduction factor of 7 using a polyethersulfone (PES) membrane having a molecular weight cut-off of 'y' Daltons. The partially concentrated supernatant, having a volume of 'z' L and a protein content of 'aa' % by weight was then adjusted to a conductivity of 'ab' mS by the addition of 2.5% calcium chloride by weight of protein, resulting in the formation of a haze. This solution was then centrifuged and/or filtered to remove precipitated material resulting in 'ac' L of a clarified, partially concentrated protein solution at a protein content of 'ad' % by weight. The clarified, partially concentrated protein solution was then further concentrated to 'ae' L by ultrafiltration using the same membrane as used for the initial concentration of the supernatant. The concentrated solution was then diafiltered on the same membrane with 'af' volumes of pH 3 RO water. The diafiltered concentrate contained 'ag' % protein by weight. With the additional protein recovered from the supernatant, the overall protein recovery of the filtered protein solution was 'ah' wt %. An aliquot of 'ai' kg of concentrate was subjected to a colour reduction step by passing it through a 'aj' L BV of granular activated carbon at a rate of 'ak' BV/hr at pH 3. The 'al' kg of GAC treated solution having reduced colour and a protein content of 'am' % by weight was then spray dried and given designation 's' C200CaC. The C200CaC had a protein content of 'an' % wt (N×6.25) d.b. The remaining 'ao' of concentrate was spray dried without further purification steps to form a final product given designation 's' C200Ca that had a protein content of 'ap' % (N×6.25) d.b.

The parameters 's' to 'ap' for two runs are set forth in the following Table VIII:

TABLE VIII

| s | BW-SD084-H27-08A | BW-SD084-I08-08A |
|---|---|---|
| t | 133 | 473 |
| u | 0.58 | 0.63 |
| v | 1.22 | 1.10 |
| w | 3.11 | 3.07 |
| x | 143 | 451 |
| y | 10,000 | 10,000 |
| z | 29 | 64 |
| aa | 2.93 | 4.29 |
| ab | 4.44 | 4.64 |
| ac | 27 |  |
| ad | 2.27 | 3.96 |
| ae | 5 | 25 |
| af | 5 | 5 |
| ag | 9.44 | 8.00 |
| ah | 63.6 | 70.7 |
| ai | 0 | 25.46 |
| aj |  | 2.5 |
| ak |  | 2.5 |
| al |  | 26.0 |
| am |  | 6.32 |
| an |  | 96.85 |
| ao | 4.6 | 0 |
| ap | 91.23 |  |

Example 5

This Example describes the production of a novel canola protein isolate in accordance with one embodiment of the invention, in which there is no acidification step.

'a' grams of canola meal was added to 'b' ml of 'c' M NaCl solution at ambient temperature and agitated for 30 minutes to provide an aqueous protein solution. The residual canola meal was removed and the resulting protein solution was clarified by centrifugation and filtration to provide 'd' ml of protein solution having a protein content of 'e' % by weight. An 'f' ml aliquot of the protein extract solution was reduced in volume to 'g' ml by concentration on a cellulose membrane having a molecular weight cutoff of 'h' Daltons. The resulting concentrated protein solution had a protein content of 'i' % by weight.

The concentrated solution at 'j' ° C. was diluted 'k' into cold RO water having a temperature 'l' ° C. A white cloud formed immediately and was allowed to settle. The upper diluting water was removed and the precipitated, viscous, sticky mass (PMM) was recovered by centrifugation. The dried PMM derived protein was found to have a protein content of 'm' % (N×6.25) d.b.

The parameters 'a' to 'm' for the run are set forth in the following Table IX:

TABLE IX

| a | 150 |
|---|---|
| b | 1500 |
| c | 0.15 |
| d | 1200 |
| e | 1.29 |
| f | 1200 |
| g | 95 |
| h | 10,000 |
| i | 11.39 |
| j | 30 |

TABLE IX-continued

| | |
|---|---|
| k | 1:15 |
| l | 4 |
| m | 103% |

The calcium chloride addition described in the present application was then carried out on the supernatant.

'n' ml supernatant was adjusted to a conductivity 'o' mS by the addition of calcium chloride from a concentrated solution. This solution was then centrifuged and/or filtered to remove precipitated phytate material resulting in 'p' ml of a reduced phytate content, clarified protein solution at a concentration of 'q' % by weight. The reduced phytate content, clarified supernatant was then reduced in volume to 'r' ml by ultrafiltration using a cellulose membrane having a molecular weight cut-off of 's' Daltons. The concentrate was then diafiltered on the same membrane with 't' volumes of water. The diafiltered concentrate contained 'u' % protein by weight and had a volume of 'v' ml. This solution was freeze dried without further purification steps to form a final product having a protein content of 'w' % (N×6.25) d.b. The parameters 'n' to 'w' for the run are set forth in the following Table X:

TABLE X

| | |
|---|---|
| n | 1400 |
| o | 9 |
| p | 1350 |
| q | 0.30 |
| r | 60 |
| s | 10,000 |
| t | 5 |
| u | 4.5 |
| v | 40 |
| w | 92.15 |

The freeze dried product was resolubilized in water at natural pH. The absorbance at 600 nm (A600) was determined as an indicator of clarity. The solution was then split in half and one half adjusted to pH 3, the other half adjusted to pH 6. The A600 on each was read again. The results obtained are set forth in the following Table XI:

TABLE XI

| | A600 | LECO Protien |
|---|---|---|
| Natural pH sample | 0.073 | 2.60 |
| pH 3 sample | 0.047 | 2.55 |
| pH 6 sample | 0.151 | 2.58 |

All samples were visually clear.

SUMMARY OF THE DISCLOSURE

In summary of this disclosure, a 2S-predominated canola protein isolate is produced of equivalent properties to the 2S-predominated canola protein isolate produced by heat treatment of supernatant from PMM formation and deposition. Modifications are possible within the scope of the invention.

What we claim is:

1. A process of preparing a canola protein isolate having a protein content of at least about 90 wt % (N×6.25) on a dry weight basis, which comprises:
adding an initial quantity of a calcium salt to supernatant from the precipitation of a canola protein micellar mass to provide conductivity of about 1 to about 3.5 and insufficient to cause precipitation of calcium phytate,
adjusting the pH of the resulting solution to about 2.0 to about 4.0 to form an acidified solution,
partially concentrating the acidified solution to a protein concentration of about 50 g/L or less,
adding a further quantity of a calcium salt to provide a conductivity of about 4 mS to about 30 mS, and to cause a precipitate to form,
removing the precipitate from the resulting solution to provide a clear pH-adjusted solution,
concentrating the clear, pH-adjusted solution to a protein content of at least about 50 g/L to produce a clear concentrated canola protein solution,
optionally diafiltering the clear canola protein solution,
optionally effecting a colour removal step, and
drying the concentrated protein solution.

2. The process of claim 1 wherein the calcium salt is calcium chloride.

3. The process of claim 1 wherein the initial quantity of calcium salt is added to provide a conductivity of about 1 to about 2 mS.

4. The process of claim 1 wherein the pH of the clear solution is adjusted to a pH of about 2.9 to about 3.2.

5. The process of claim 1 wherein the further quality of calcium salt is added to provide a conductivity of about 4 to about 10 mS.

6. The process of claim 1 wherein the clear pH-adjusted solution is concentrated to a concentration of about 50 to about 500 g/L.

7. The process of claim 6 wherein the concentration is about 100 to about 350 g/L.

8. The process of claim 1 wherein the clear concentrated canola protein solution is diafiltered with volumes of pH 3 water.

9. The process of claim 1 wherein said colour removal step is a granular activated carbon treatment.

10. The process of claim 1 wherein the calcium salt is calcium chloride, the initial quantity of calcium salt is added to provide a conductivity of about 4 to about 10 mS, and the clear pH-adjusted solution is concentrated to a concentration of about 50 to about 500 g/L.

11. A process of preparing a canola protein isolate having a protein content of at least about 90 wt % (N×6.25) on a dry weight basis, which comprises:
adding a calcium salt to supernatant from the precipitation of a canola protein micellar mass to provide a conductivity of about 5 mS to about 30 mS to cause precipitation of calcium phytate from the supernatant,
adjusting the pH of the resulting solution without removal of the calcium phytate precipitate to about 2.0 to about 4.0 to dissolve the precipitate and form a clear pH-adjusted solution,
concentrating the clear pH-adjusted solution to a protein content of at least about 50 g/L to produce a clear concentrated canola protein solution,
optionally diafiltering the clear concentrated canola protein solution,
optionally effecting a colour removal step, and
drying the concentrated protein solution.

12. The process of claim 11 wherein the calcium salt is calcium chloride.

13. The process of claim 11 wherein the conductivity is from about 8 to about 10 mS.

14. The process of claim 11 wherein the pH of the clear solution is adjusted to a pH of about 2.9 to about 3.2.

15. The process of claim 11 wherein the clear pH-adjusted solution is concentrated to a protein content of about 100 to about 500 g/L.

16. The process of claim 15 wherein the concentration is about 100 to about 350 g/L.

17. The process of claim 11 wherein the clear concentrated canola protein solution is diafiltered with volumes of pH 3 water.

18. The process of claim 11 wherein said colour removal step is a granular activated carbon treatment.

19. The process of claim 11 wherein the calcium salt is calcium chloride, the conductivity is from about 8 to about 10 mS, the pH of the clear solution is adjusted to a pH of about 2.9 to about 3.2 and the optionally pH-adjusted clear solution is concentrated to a concentration of about 50 to about 500 g/L.

20. A process of preparing a canola protein isolate having a protein content of at least about 90 wt % (N×6.25) on a dry weight basis, which comprises:
  partially concentrating the supernatant from the precipitation of a canola protein micellar mass to a concentration of about 50 g/L or less,
  adding a calcium salt to the partially concentrated supernatant to provide a conductivity of about 2 mS to about 30 mS to precipitate calcium phytate from the partially concentrated supernatant,
  adjusting the pH of the resulting solution without removal of the calcium phytate precipitate to about 2.0 to about 4.0 to dissolve the precipitate and form a clear pH-adjusted solution,
  concentrating the pH-adjusted clear solution to a protein content of at least about 50 g/L to produce a clear concentrated canola protein solution,
  optionally diafiltering the clear canola protein solution,
  optionally effecting a colour removal step, and
  drying the concentrated protein solution.

21. The process of claim 20 wherein the calcium salt is calcium chloride.

22. The process of claim 20 wherein the conductivity is about 4 to about 10 mS.

23. The process of claim 20 wherein the pH of the clear solution is adjusted to a pH of about 2.9 to about 3.2.

24. The process of claim 20 wherein the pH-adjusted clear solution is concentrated to a protein content of about 100 to about 500 g/L.

25. The process of claim 24 wherein the concentration is about 100 to about 350 g/L.

26. The process of claim 20 wherein the clear concentrated canola protein solution is diafiltered with volumes of pH 3 water.

27. The process of claim 20 wherein said colour removal step is a granular activated carbon treatment.

28. The process of claim 20 wherein the calcium salt is calcium chloride, the conductivity is from about 4 to about 10 mS, the pH of the clear solution is adjusted to a pH of about 2.9 to about 3.2 and the optionally pH-adjusted clear solution is concentrated to a concentration of about 50 to about 500 g/L.

29. A process of preparing a canola protein isolate having a protein content of at least about 90 wt % (N×6.25) on a dry weight basis, which comprises:
  concentrating supernatant from the precipitation of a canola protein micellar mass to a protein content of at least about 50 g/L to produce a concentrated supernatant,
  adding a calcium salt to the concentrated supernatant to provide a conductivity of about 2 to about 30 mS to cause precipitation of calcium phytate,
  adjusting the pH of the resulting solution without removal of the calcium phytate precipitate to about 2.0 to about 4.0 to dissolve the precipitate and form a clear pH-adjusted solution,
  optionally diafiltering the clear pH-adjusted solution,
  optionally effecting a colour removal step, and
  drying the clear pH-adjusted protein solution.

30. The process of claim 29 wherein the optionally pH-adjusted clear solution is concentrated to a concentration of about 50 to about 500 g/L.

31. The process of claim 30 wherein the concentration is about 100 to about 350 g/L.

32. The process of claim 29 wherein the calcium salt is calcium chloride.

33. The process of claim 29 wherein the conductivity is from about 4 to about 10 mS.

34. The process of claim 29 wherein the pH of the clear solution is adjusted to a pH of about 2.9 to about 3.2.

35. The process of claim 29 wherein the clear concentrated canola protein solution is diafiltered with volumes of pH 3 water.

36. The process of claim 29 wherein said colour removal step is a granular activated carbon treatment.

37. The process of claim 29 wherein the calcium salt is calcium chloride, the conductivity is from about 4 to about 10 mS, the pH of the clear solution is adjusted to a pH of about 2.9 to about 3.2 and the optionally pH-adjusted clear solution is concentrated to a concentration of about 50 to about 500 g/L.

* * * * *